United States Patent [19]

Bellas et al.

[11] 4,294,991
[45] Oct. 13, 1981

[54] PROCESS FOR MONOALKYLATION OF DIHYDRIC PHENOLS

[75] Inventors: Michael Bellas, Wigan; Robert Cahill, Kirkby, both of England

[73] Assignee: Eastman Kodak Company, Rochester, N.Y.

[21] Appl. No.: 78,123

[22] Filed: Sep. 24, 1979

Related U.S. Application Data

[63] Continuation of Ser. No. 904,683, May 10, 1978, abandoned, which is a continuation-in-part of Ser. No. 748,036, Dec. 6, 1976, abandoned.

[51] Int. Cl.³ .................... C07C 43/178; C07C 43/00
[52] U.S. Cl. .................................... 568/650; 568/651
[58] Field of Search ..................... 568/650, 804, 651

[56] References Cited

U.S. PATENT DOCUMENTS

| | | | |
|---|---|---|---|
| 833,605 | 1/1906 | Julius | 568/650 |
| 3,895,076 | 7/1975 | Bauer et al. | 568/650 |
| 4,025,566 | 5/1977 | Nagar et al. | 568/650 |
| 4,153,810 | 5/1979 | Neumann et al. | 568/650 |

*Primary Examiner*—Werren B. Lone
*Attorney, Agent, or Firm*—J. Frederick Thomsen; Daniel B. Reece, III

[57] ABSTRACT

A process for the preparation of a monoalkyl ether having the formula

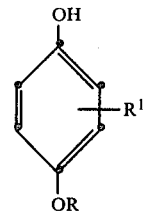

wherein R is an alkyl radical having 1 to 18 carbon atoms or $C_2H_5-O-CH_2CH_2-$ and $R^1$ is hydrogen or an alkyl radical having 1 to 4 carbon atoms, which comprises reacting a compound having the formula R—OH with a mixture of a compound having the formula

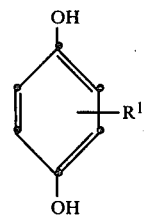

and a compound having the formula

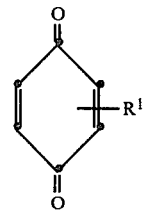

in the presence of an acid dehydration catalyst, wherein the weight ratio of II:III is from 5:1 to 20:1.

16 Claims, No Drawings

PROCESS FOR MONOALKYLATION OF DIHYDRIC PHENOLS

This is a continuation of application Ser. No. 904,683 filed May 10, 1978, which is a CIP of application Ser. No. 748,036 filed Dec. 6, 1976, now abandoned.

This invention relates to the preparation of monoalkyl ethers of hydroquinones.

According to the present invention, there is provided a process for the preparation of a monoalkyl ether having the formula

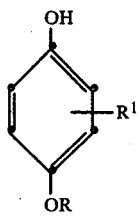

I wherein R is an alkyl radical having 1 to 18 carbon atoms or $C_2H_5-O-CH_2CH_2-$, and $R^1$ is hydrogen or an alkyl radical having 1 to 4 carbon atoms, which comprises reacting a compound having the formula R-OH with a mixture of a compound having the formula

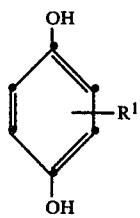

II and a compound having the formula

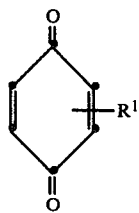

III in the presence of an acid dehydration catalyst, wherein the weight ratio of II:III is from 5:1 to 20:1.

The alkyl radicals representative of R and $R^1$ may be branched or unbranched. Examples of alkyl radicals representative of R are methyl, ethyl, t-butyl, propyl, decyl, octadecyl, pentyl, and the like. Preferably, R is selected from methyl, ethyl, isopropyl, isobutyl, n-butyl, sec.-butyl, and ethoxy ethyl. Examples of groups representative of R are hydrogen, methyl, ethyl, propyl, isopropyl, t-butyl, isobutyl, and the like. Preferably, $R^1$ is hydrogen or t-butyl. Therefore, representative examples of the compounds identified as compound II are hydroquinone, t-butyl hydroquinone, methyl hydroquinone, etc.

It will often be possible to carry out the process of the present invention at room temperature, but more conveniently the process will be performed under reflux.

Preferably, the weight ratio of Compound II to Compound III is from 10:1 to 20:1.

If desired, the compound of formula III may be generated in situ from the compound of formula II; for example, by the use of an oxidant, e.g. air or manganese dioxide, or by electrochemical oxidation.

The monoalkyl ether which is obtained when, R is methyl and $R^1$ is tert-butyl is butylated hydroxyanisole, which is of value as an antioxidant.

The amount of the alcohol (ROH) is not critical, but its practical limits will be determined by the solubility of the compounds II and III therein. If the amount of compound II present is high with respect to the alcohol, then sufficient compound III will not enter solution, and the effective ratio of II:III becomes too high. Generally, however, the preferred amount of alcohol is 5 to about 35 moles per mole of compound II.

Suitable acid dehydration catalysts useful in the practice of this invention include concentrated sulphuric acid and p-toluene sulphonic acid. Sulphonated styrene resin acids, such as those available under the trade name "Amberlite", may also be used. The preferred acid dehydration catalyst is concentrated sulphuric acid. When sulphuric acid is used, the acid should be neutralized at the end of the reaction with an alkali metal hydroxide such as sodium hydroxide or potassium hydroxide. The precipitated sodium sulphate can be removed by filtration. Neutralization is usually necessary if p-toluene sulphonic acid is used, but the sulphonated styrene resin acids can be removed by simple filtration.

The amount of concentrated sulphuric acid which is used can be varied, for example, up to 5 moles per mole of compound II. The preferred amount is from 0.1 to 4.5 moles per mole of compound II.

After the acid dehydration catalyst has been removed, the product can be separated by distillation.

This invention will be further illustrated by the following examples, although it will be understood that these examples are included merely for purposes of illustration and are not intended to limit the scope of the invention.

EXAMPLES 1 to 6

Hydroquinone (10 g.) and benzoquinone (1 g.) dissolved in each of the alcohols listed in Table I below (100 ml.), together with concentrated sulphuric acid (2 g.), were stirred at room temperature for 16 hours. Each reaction mixture was neutralized with sodium hydroxide, and the precipitated sodium sulphate was filtered off. The filtrate was examined by gas-liquid chromatography to measure the extent of the conversion of hydroquinone to hydroquinone monalkyl ether. The results are given in Table I.

TABLE I

| Alcohol (R—OH) | Conversion of Hydroquinone to Hydroquinone Monoalkyl Ether (%) |
|---|---|
| 1. Ethanol | 40 |
| 2. Isopropanol | 75 |
| 3. Isobutanol | 65 |
| 4. 2-Ethoxyethanol | 35 |
| 5. n-Butanol | 80 |
| 6. sec-Butanol | 60 |

EXAMPLES 7 to 18

Mixtures of hydroquinone and benzoquinone in varying proportions in methanol (15 ml.) were treated with various amounts of concentrated sulphuric acid and stirred overnight at room temperature. The reaction mixture was neutralized with potassium hydroxide and filtered, and the filtrate was examined by gas-liquid chromatography to determine the extent of the conversion of hydroquinone to hydroquinone monomethyl ether. The amount of any hydroquinone dimethyl ether which was present was measured.

The quantities of reactants and the results are shown in Table II.

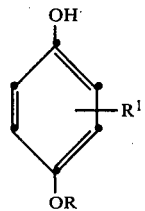

I

TABLE II

| Exp. No. | B.Q. (g) | H.Q. (g) | H₂SO₄ (g) | MeOH (mls) | Yield HQDME(1) | Yield HQMME(1) | Yield* HQMME | Conversion |
|---|---|---|---|---|---|---|---|---|
| 1 | 1.67 | 8.33 | 10.0 | 50 | 3.0% | 77% | 77% | 100% |
| 2 | 1.67 | 8.33 | 2.0 | 50 | 1.4% | 73% | 73% | 100% |
| 3 | 1.67 | 8.33 | 1.0 | 50 | — | 100% | 60% | 60% |
| 4 | 1.0 | 9.0 | 10.0 | 50 | 0.7% | 80% | 80% | 99% |
| 5 | 1.0 | 9.0 | 2.0 | 50 | — | 82% | 75% | 92% |
| 6 | 1.0 | 9.0 | 1.0 | 50 | — | 89% | 67% | 75% |
| 7 | 0.67 | 9.33 | 10.0 | 50 | — | 80% | 80% | 100% |
| 8 | 0.67 | 9.33 | 2.0 | 50 | — | 100% | 66% | 65% |
| 9 | 0.67 | 9.33 | 1.0 | 50 | — | 100% | 58% | 50% |
| 10 | 0.5 | 9.5 | 10.0 | 50 | — | 80% | 78% | 98% |
| 11 | 0.5 | 9.5 | 2.0 | 50 | — | 100% | 58% | 50% |
| 12 | 0.5 | 9.5 | 1.0 | 50 | — | 100% | 54% | 45% |

(1)hydroquinone dimethyl ether
(2)hydroquinone monomethyl ether
*calculated on the assumption that the unconverted hydroquinone is not recovered and used again

EXAMPLE 19

Example 7 was carried out on a larger scale, using 200 g of hydroquinone, 40 g of benzoquinone, 240 g of concentrated sulphuric acid and 1,200 ml of methanol. The reaction mixture was neutralized with potassium hydroxide and filtered, and the filtrate was distilled at reduced pressure (2 mm Hg). The fraction boiling at 99° to 102° C. was collected (168.5 g, 62% conversion of hydroquinone to hydroquinone monomethyl ether). The product was shown by infrared and nuclear magnetic resonance spectra to contain no hydroquinone dimethyl ether.

EXAMPLE 20

Hydroquinone (18 g) and benzoquinone (2 g) in methanol (100 ml) with p-toluene sulphonic acid (5 g) were heated under reflux for 6 hours. Samples taken at 3 and 6 hours were analyzed by gas-liquid chromatography and found to have the compositions indicated in Table III.

TABLE III

| Sample | Benzoquinone | Hydroquinone Monomethyl Ether | Hydroquinone |
|---|---|---|---|
| After 3 hours | 0.12 g | 14.6 g | 3.6 g |
| After 6 hours | 0.00 g | 15.8 g | 2.8 g |

The conversion was thus complete after 6 hours under reflux.

The invention has been described in detail with particular reference to preferred embodiments thereof, but it will be understood that variations and modifications can be effected within the spirit and scope of the invention.

We claim:

1. A process for the preparation of a monoalkyl ether having the formula wherein R is an alkyl radical having 1 to 18 carbon atoms or $C_2H_5-O-CH_2CH_2-$ and $R^1$ is hydrogen or an alkyl radical having 1 to 4 carbon atoms, which comprises reacting a compound having the formula R-OH with a mixture of a compound having the formula

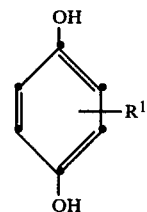

II and a compound having the formula

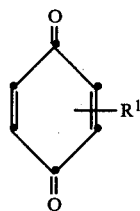

III in the presence of an acid dehydration catalyst, wherein the weight ratio of II:III is from 5:1 to 20:1.

2. Process of claim 1 wherein the weight ratio of compound II to III is from 10:1 to 20:1.

3. Process of claim 2 wherein the acid dehydration catalyst is selected from sulfuric acid, sulfonated styrene resin acids and p-toluenesulfonic acid.

4. Process of claim 1 wherein R is methyl, ethyl, isopropyl, isobutyl, n-butyl, sec-butyl, or 2-ethoxyethyl; and $R^1$ is hydrogen, methyl, ethyl, or t-butyl.

5. Process of claim 2 wherein R is methyl, ethyl, isopropyl, isobutyl, n-butyl, sec-butyl, or 2-ethoxyethyl; and $R^1$ is hydrogen, methyl, ethyl or t-butyl.

6. Process of claim 3 wherein R is methyl, ethyl, isopropyl, isobutyl, n-butyl, sec-butyl, or 2-ethoxyethyl; and $R^1$ is hydrogen, methyl, ethyl or t-butyl.

7. Process of claim 1 wherein compound II is hydroquinone and compound III is benzoquinone, and the alcohol is methanol.

8. Process of claim 2 wherein compound II is hydroquinone and compound III is benzoquinone, and the alcohol is methanol.

9. Process of claim 3 wherein compound II is hydroquinone and compound III is benzoquinone, and the alcohol is methanol.

10. Process of claim 4 wherein $R^1$ is t-butyl and R is methyl.

11. Process of claim 1 wherein the acid catalyst is a sulfonated styrene resin acid.

12. Process of claim 11 wherein the weight ratio of compounds II to III is from 10:1 to 20:1.

13. Process of claim 12 wherein R is methyl, ethyl, isopropyl, isobutyl, n-butyl, sec-butyl or 2-ethoxyethyl; and $R^1$ is hydrogen, methyl, ethyl or t-butyl.

14. Process of claim 13 wherein compound II is hydroquinone, compound III is benzoquinone and the alcohol is methanol.

15. Process of claim 3 wherein the process is carried out at a temperature in the range of room temperature to reflux temperature.

16. Process of claim 9 wherein the process is carried out at a temperature in the range of room temperature to reflux temperature.

* * * * *